US011160478B2

(12) United States Patent
Piacentini et al.

(10) Patent No.: US 11,160,478 B2
(45) Date of Patent: *Nov. 2, 2021

(54) BLOOD AND BIOLOGICAL SAMPLE COLLECTION DEVICE AND METHOD

(71) Applicant: SEDIA BIOSCIENCES CORPORATION, Beaverton, OR (US)

(72) Inventors: Stephen Carl Piacentini, Portland, OR (US); Ronald William Mink, West Linn, OR (US); Paul Robert Smith, Washougal, WA (US)

(73) Assignee: SEDIA BIOSCIENCES CORPORATION, Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/995,908

(22) Filed: Jun. 1, 2018

(65) Prior Publication Data

US 2019/0029581 A1    Jan. 31, 2019

Related U.S. Application Data

(63) Continuation of application No. 15/356,226, filed on Nov. 18, 2016, now Pat. No. 9,986,944, which is a
(Continued)

(51) Int. Cl.
*A61B 5/15* (2006.01)
*B01L 3/00* (2006.01)
(Continued)

(52) U.S. Cl.
CPC ...... *A61B 5/150358* (2013.01); *B01L 3/5023* (2013.01); *G01N 33/48771* (2013.01);
(Continued)

(58) Field of Classification Search
CPC ...... A61B 5/150358; A61B 2562/0295; A61B 5/150022; A61B 5/150755;
(Continued)

(56) References Cited

U.S. PATENT DOCUMENTS 3,552,928 A    1/1971   Fetter
4,477,575 A    10/1984  Vogel et al.
(Continued)

OTHER PUBLICATIONS

European Patent Office, International Search Report and Written Opinion for International Application No. PCT/US2015/029631, dated Aug. 28, 2015.
(Continued)

*Primary Examiner* — Samuel P Siefke
(74) *Attorney, Agent, or Firm* — Rimon, P.C.

(57) ABSTRACT

Specially designed collection strips and their processing. By using specially designed collection strips, having a backer and one or more absorbent pads, in conjunction with a unique processing method, the processes of analyzing biological samples such as blood, or the like, may be done efficiency with the elimination of cross contamination risk. Identification of the sample stays with the sample throughout the process as it resides on the collection strip. The strip absorbs a known volume. The sample with identification is placed directly in an elution solution, without mechanically separating the sample from its identification information. Elimination of the need for mechanical separation tends to reduce cross contamination, as well as reducing sample processing time.

10 Claims, 7 Drawing Sheets

Related U.S. Application Data continuation-in-part of application No. 14/706,240, filed on May 7, 2015, now abandoned.

(60) Provisional application No. 61/990,482, filed on May 8, 2014.

(51) Int. Cl.
*G01N 33/487* (2006.01)
*G01N 33/49* (2006.01)
*G01N 1/28* (2006.01)
*G01N 1/40* (2006.01)

(52) U.S. Cl.
CPC ...... *G01N 33/491* (2013.01); *A61B 5/150022* (2013.01); *A61B 5/150755* (2013.01); *A61B 2562/0295* (2013.01); *A61B 2562/08* (2013.01); *B01L 3/505* (2013.01); *B01L 2300/021* (2013.01); *B01L 2300/069* (2013.01); *B01L 2300/0825* (2013.01); *G01N 1/28* (2013.01); *G01N 2001/4088* (2013.01); *Y10T 436/255* (2015.01); *Y10T 436/2575* (2015.01); *Y10T 436/25125* (2015.01)

(58) Field of Classification Search
CPC ......... A61B 2562/08; G01N 33/48771; G01N 33/491; G01N 1/28; G01N 2001/4088; B01L 3/5023; B01L 3/505; B01L 2300/021; B01L 2300/069; B01L 2300/0825; Y10T 436/2575; Y10T 436/255; Y10T 436/25125
See application file for complete search history.

(56) References Cited

U.S. PATENT DOCUMENTS

| | | | |
|---|---|---|---|
| 4,883,764 | A | 11/1989 | Kloepfer |
| 5,460,057 | A | 10/1995 | Ostrup |
| 5,766,552 | A | 6/1998 | Doshi et al. |
| 5,783,759 | A | 7/1998 | Wielinger et al. |
| 6,036,659 | A | 3/2000 | Ray et al. |
| 6,106,732 | A | 8/2000 | Johnston et al. |
| 6,231,815 | B1 | 5/2001 | Bainczyk et al. |
| 8,685,749 | B2 | 4/2014 | Shoemaker et al. |
| 9,040,236 | B2 | 5/2015 | Hill et al. |
| 9,986,944 | B2 | 6/2018 | Piacentini et al. |
| 2003/0013121 | A1 | 1/2003 | Khan |
| 2013/0116597 | A1 | 5/2013 | Rudge et al. |
| 2014/0373644 | A1 | 12/2014 | Iraneta et al. |
| 2015/0320347 | A1 | 11/2015 | Piacentini et al. |

OTHER PUBLICATIONS

Office Action for U.S. Appl. No. 14/706,240, dated Nov. 3, 2015, 12 pages.
Response to Office Action for U.S. Appl. No. 14/706,240, dated May. 3, 2016, 18 pages.
Office Action for U.S. Appl. No. 14/706,240, dated May. 20, 2016, 15 pages.
Abandonment for U.S. Appl. No. 14/706,240, dated Dec. 7, 2016, 3 pages.
Office Action for U.S. Appl. No. 15/356,226, dated Apr. 7, 2017, 15 pages.
Response to Office Action for U.S. Appl. No. 15/356,226, dated Sep. 7, 2017, 25 pages.
Office Action for U.S. Appl. No. 15/356,226, dated Sep. 12, 2017, 4 pages.
Final Rejection for U.S. Appl. No. 15/356,226, dated Oct. 6, 2017, 14 pages.
Office Action Appendix for U.S. Appl. No. 15/356,226, dated Oct. 10, 2017, 6 pages.
Applicant Initiated Interview Summary for U.S. Appl. No. 15/356,226, dated Oct. 16, 2017, 3 pages.
Response to Office Action for U.S. Appl. No. 15/356,226, dated Jan. 31, 2018, 14 pages.
Notice of Allowance for U.S. Appl. No. 15/356,226, dated Feb. 9, 2018, 7 pages.
International Search Report for international patent application PCT/US2015/029631 (WO2015171859), dated Aug. 28, 2015, 4 pages.
Written Opinion of the International Searching Authority for international patent application PCT/US2015/029631 (WO2015171859), dated Aug. 28, 2015, 5 pages.
International Preliminary Report on Patentability for international patent application PCT/US2015/029631 (WO2015171859), dated Nov. 8, 2016, 6 pages.

BLOOD AND BIOLOGICAL SAMPLE COLLECTION DEVICE AND METHOD

CROSS-REFERENCE TO RELATED APPLICATION

This application is a continuation of U.S. patent application Ser. No. 15/356,226, filed Nov. 18, 2016, now allowed, which is a continuation-in-part of U.S. patent application Ser. No. 14/706,240, filed May 7, 2015, now abandoned, which claims the benefit of U.S. Provisional Patent Application No. 61/990,482, filed May 8, 2014, the contents of which are hereby incorporated by reference.

TECHNICAL FIELD

This description relates generally to the collection and testing of biological materials and more specifically to dry collection and testing of biological samples including blood.

BACKGROUND

Biological samples and in particular, exemplary blood samples may be tested for various analytes usually by collecting it on paper or a card, allowing it to dry, and then sending it to a lab for processing. Alternatively, liquid samples collected in vials and typically refrigerated may also be used. The paper is typically in the form of a card in which a few drops of blood drawn by a lancet is applied and on which identifying information may be recorded. In the lab, the spot containing the sample may be punched out from the card, typically in a disk shape. The blood may be released from the punch out from the card by application of a saline solution, and the solution containing the blood may then be subjected to the desired lab testing.

In the use of collection vials, the sample may be removed from the vial, typically with a pipette, or similar tube. Pipettes are a non-planar structure, typically consisting of a pointed tube structure into which liquid may be drawn into by suction, and released onto a sample material, by releasing the vacuum created by the suction. Such a system tends to be mechanically complex, and is not easy to construct. Accordingly, a simple planar collection device that does not require the application of suction to collect a sample would be desirable. Also, such vial and pipet systems typically utilize racks to store the vials, which is a further mechanical complexity in current sample processing methods.

Testing of dried blood may be advantageously used in testing for infectious diseases, home testing by consumers and the like. This type of sample collection allows samples to be easily collected in the field and transported, typically without refrigeration, as would be needed with a liquid blood specimen. In the lab, a portion of the card containing the sample may be tested. Unfortunately, the process of detaching a portion of a sample from a card typically calls for extra processing of the sample card—typically performed manually by a lab technician. This operation also presents an opportunity for cross contamination from instruments used, so elimination of having to punch out a portion of the card would be desirable. For an individual test, the current approach may be satisfactory. However, in testing large numbers of samples, such as during an epidemic, quick testing with a minimum of handling is called for. Accordingly, developing improved devices for the collection of blood and other biological samples which are subsequently dried, and their later processing may be desirable to make sample collection, and lab processing, —especially automated processing of large numbers of samples—more efficient.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The present example provides an alternative to the processing of dried blood spot cards. By using specially designed collection strips, having a backer and one or more absorbent pads, in conjunction with a unique processing method, the processes of analyzing biological samples such as blood, or the like may be done efficiently with the elimination of cross contamination risk, as common instruments used to handle discs are not used. In particular, the specially designed test strips do not require punching and/or folding in processing samples collected thereon. Identification of the sample stays with the sample throughout the process as it resides on the collection strip. The strip absorbs a known volume. The sample with identification is placed directly in an elution solution, without mechanically separating the sample from its identification information. Elimination of the need for mechanical separation tends to reduce the known mechanism of cross contamination (especially prevalent in DNA sample testing) since there is no use of common instruments in handling samples, as well as reducing sample processing time.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The examples below describe unique collection strips and a method of processing the unique collection strips that allow increased efficiency and throughput in testing. Although the present examples are described and illustrated herein as being implemented in an exemplary single sample collection system, primarily for blood, the system described is provided as an example and not a limitation. As those skilled in the art will appreciate, the present examples are suitable for application in a variety of different types of biological samples other than blood, and in automated systems, including those for testing multiple samples.

The unique collection strips described herein are an alternative to conventional dried blood spot cards. The unique collection strips described herein incorporate a strip backing with one or more absorbent pads disposed at the end of the strip which may, or may not, be treated and may serve multiple purposes. The collection strips may be stored in dry form, and one of their uses is to collect and retain a specimen of blood, serum or plasma for the purposes of stabilizing the sample, transporting it via a stable matrix to another location (including by courier, mail, etc.) and subsequent extraction/elution into a suitable sample buffer. The extracted material in the sample buffer can then be tested in a suitable diagnostic test in a laboratory for the analyte of interest.

Treatments on the absorbent pads and pad materials may be included to filter or retain red blood cells, separate the red blood cells from the serum/plasma component, facilitate elution of the specific analyte, retain other undesirable components of the sample from the eluent (e.g., fibrin or fibrinogen retained while allowing elution of fibrinogen degradation products.) Assays may also be performed on material actively, or passively bound, to any pad/surface in the device.

The unique collection strips described herein address the desirability of having a dried blood, plasma or serum spot collection type device (but its uses are also applicable to other clinical body fluid specimens, including but not limited to saliva, oral fluid, urine, tears, sweat, nasal, vaginal/genital secretions or washes, fecal specimens, sputum, etc.) enabling transport of the specimen in dried form. In addition, such a collection strip may have other non-biological uses for example: sampling water from a lake for pollutants, reservoirs for bacteria, gasoline to verify octane level, and the like. Dried form typically provides not only a more stable specimen, not requiring specialized (e.g., cold or ice) storage during transit, but also avoids the obvious problems of transporting a liquid specimen (e.g., spillage, risk of leakage from packaging, bio hazardous contamination, etc.).

However, unlike conventional "dried blood spot cards", the end user at a laboratory does not have to "punch" out a paper disc, manipulate the disc with forceps so that it can be placed in an extraction tube, risk getting the disc trapped in the paper punch, or easily dropped to the floor. Also, using forceps and a paper punch can contribute to possible punch-to-punch cross contamination of samples.

Finally, the risk of losing, or the misidentification of punched out samples, can be greater since sample identification does not stay with the punch out during processing, as it does with the unique examples described herein. Furthermore, unlike conventional discs, the unique collection strips described herein can be easily inserted into an ordinary extraction tube, and after elution of analyte of interest, easily be removed without use of forceps. Eluted samples can be transferred quickly into a titertube layout, facilitating the processing of large numbers of dried samples using microtiter plate assays, such as exemplary ELISAs.

Figure 1:
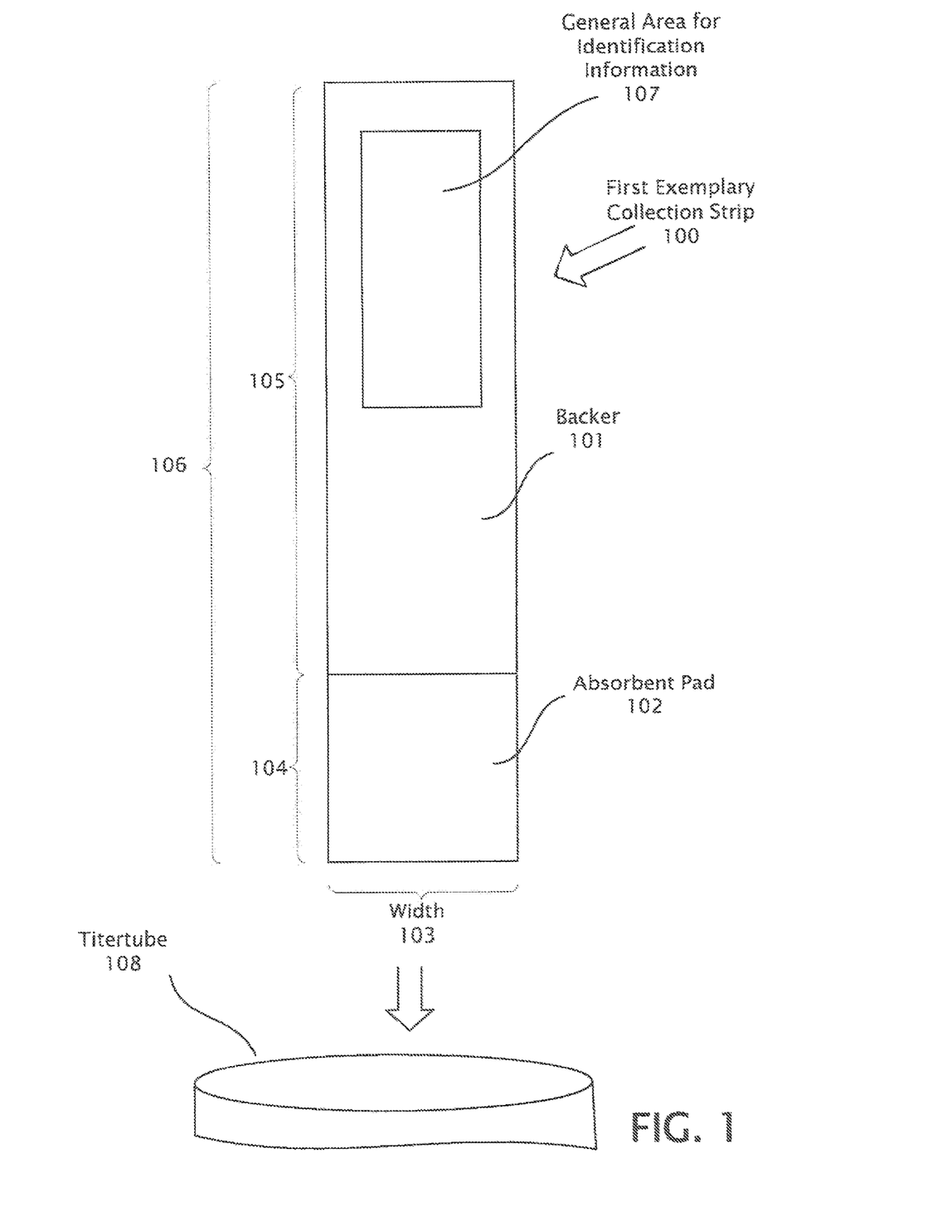
FIG. 1 is a diagram showing a front view of a first exemplary collection strip having a single pad.

FIG. 1 is a diagram showing a front view of a first exemplary collection strip having a single pad 100. The collection strip is a specially constructed lateral flow collection strip. In particular, the examples of the unique collection strip, and the methods for processing samples collected on them described herein, do not require folding or punching of this uniquely constructed collection strip. In overall appearance the first exemplary collection strip 100, may include a flat strip or backer piece 101 that is a flat strip typically solid and without cavities or holes inside of it, that is typically cut from sheet stock material, with a Pad 102 at one end. The backer shape is generally elongate 106, and rectangular. The width 103 of the first exemplary collection strip 100 may be selected to fit into various sized receptacles 108 such as titer tubes, or the like. Exemplary widths 103 may include 3 mm, 5 mm, 10 mm, 15 mm or equivalent width strips. In addition, absorbent pads may be placed on just one side of the backer, or both sides of the backer to increase available capacity.

Labeling 107 may be disposed on the backer 101, which also serves to provide space for recordation of identification information, so that sample tracking is improved, as identification stays with the sample during processing. Entry of the sample ID, a bar code, special instructions or the like may be recorded here at 107. Such a marked dried blood collection strip 100 can also be easily archived for future testing just like a traditional dried blood spot card.

The overall shape of the backer 101 may typically be a rectangular flat solid strip of liquid resistant flexible material, however its shape may equivalently have rounded corners, may be made up of compound shapes, may be oval, or of any other convenient shape to support the pad 102, provide a labeling area 107, facilitate machine processing, or the like. Backer 101 may also include one or more apertures (not shown) to facilitate dispensing and storage of strips. And adjacent strips may also be coupled via perforations to a sheet or book containing a plurality of collection strips from which an individual strip 100 may be detached or dispensed prior to sample collection.

The backer 101 may be made from a suitable flat, flexible non porous material (e.g., plastic, paper, vinyl, etc.) 101, suitable to act as a handle and to support the absorbent pad used to collect the sample.

At the opposite end of the backer 101 from the identification area 107, is an absorbent pad 102 used to capture the sample. The absorbent pad 102 may be disposed on one side of the backer and is coupled to it by conventional methods. In alternative examples (not shown) a pad may be disposed on both sides of the backer 101, with such placement typically substantially opposite absorbent pad 102.

The absorbent pad 102 material may be composed of any of a number of materials suitable for affixing to the backing 101 and capable of absorbing a desired clinical specimen. Suitable materials include but are not limited to cellulose (e.g., cellulose sold under the trademark WHATMAN® #903 paper), polyester (e.g., polyester sold under the trademark WHATMAN® 165), glass fiber (e.g., glass fiber sold under the trademark WHATMAN® 33 Glass), or the like. In particular, in examples of absorbent pads, it may not be suitable to substitute glass fibre for cellulose since the cellulose may have absorption characteristics superior to those of glass for a particular sample type being collected. The material of the absorbent pad 102 may be treated with various materials that may facilitate elution of sample material from the pad such as detergents, surfactants, blocking agents, or the like.

The pad is generally rectangular or square, but can be designed with any width 103 and pad height 104. It may be desirable to pick an appropriate sized pad to control the amount of sample collected by utilizing a calculated pad volume. Equivalently other pad shapes to collect a desired sample volume may be utilized such as rectangular, square, oval, circular or the like. Equivalently, the absorbent pad 102 of whatever shape selected need not extend all the way to the edges of the backer 101 as shown in the exemplary figure. However, the pad may typically extend to the bottom edge of the backer 101 or slightly beyond to facilitate absorption upon contact.

The absorbent pad material 102 used in the first exemplary blood collection strip allows for the quick and thorough release of all analytes, small molecules, antigens, antibodies, and nucleic acid during subsequent processing. In contrast, the cellulose material typically used in conventional blood collection cards notoriously binds proteins, small molecules and nucleic acids. This binding tends to reduce the sensitivity of the system, necessitating the collection and use of greater amounts of specimen to compensate for the decreased inherent sensitivity.

It is also expedient to select a width 103 to enable the strip to fit into existing testing apparatus configurations (e.g., titertubes 108). This selection helps facilitate handling at the receiving laboratory—especially when testing multiple samples.

The first exemplary collection strip 100 provides an efficient way to collect a blood (or other) specimen from a patient. In contrast, the use of conventional collection cards requires either awkwardly pressing the card itself onto the blood or using pipettes to transfer blood to the card. The first exemplary collection strip 100 requires no pipettes because the collected blood quickly wicks up the strip when the strip is contacted with the sample. In fact, the wicking process is unique to the exemplary test strips, since wicking in a pipet system would be undesirable as suction is used to collect and dispense samples. Wicking in a pipet system may tend to interfere with the dispensing of a sample from a pipet as a wicking or capillary action would tend to keep the sample in the pipette.

The first exemplary collection strip 100 collects a consistent and uniform amount of blood. The amount of blood that is collected can be predetermined by how many and which specific sized first exemplary collection strip 100 is used. For example, the 3 mm first exemplary collection strip 100 may be configured to collect 15 ml of blood which is roughly equivalent to that contained in a 6 mm dried blood spot punch sample. Applications that call for specific concentrations of blood are facilitated by the use of the first exemplary collection strip 100 as compared to the typically inconsistent and unknown amount of blood collected on a typical collection card.

Specimen identification 107, which may be recorded on the first exemplary collection strip 100, remains attached as a fixed linked to the specimen throughout the elution process described below. In contrast, the link between specimen ID and the dried specimen is lost as soon as the dried blood spot is punched out of the collection card.

Figure 2:
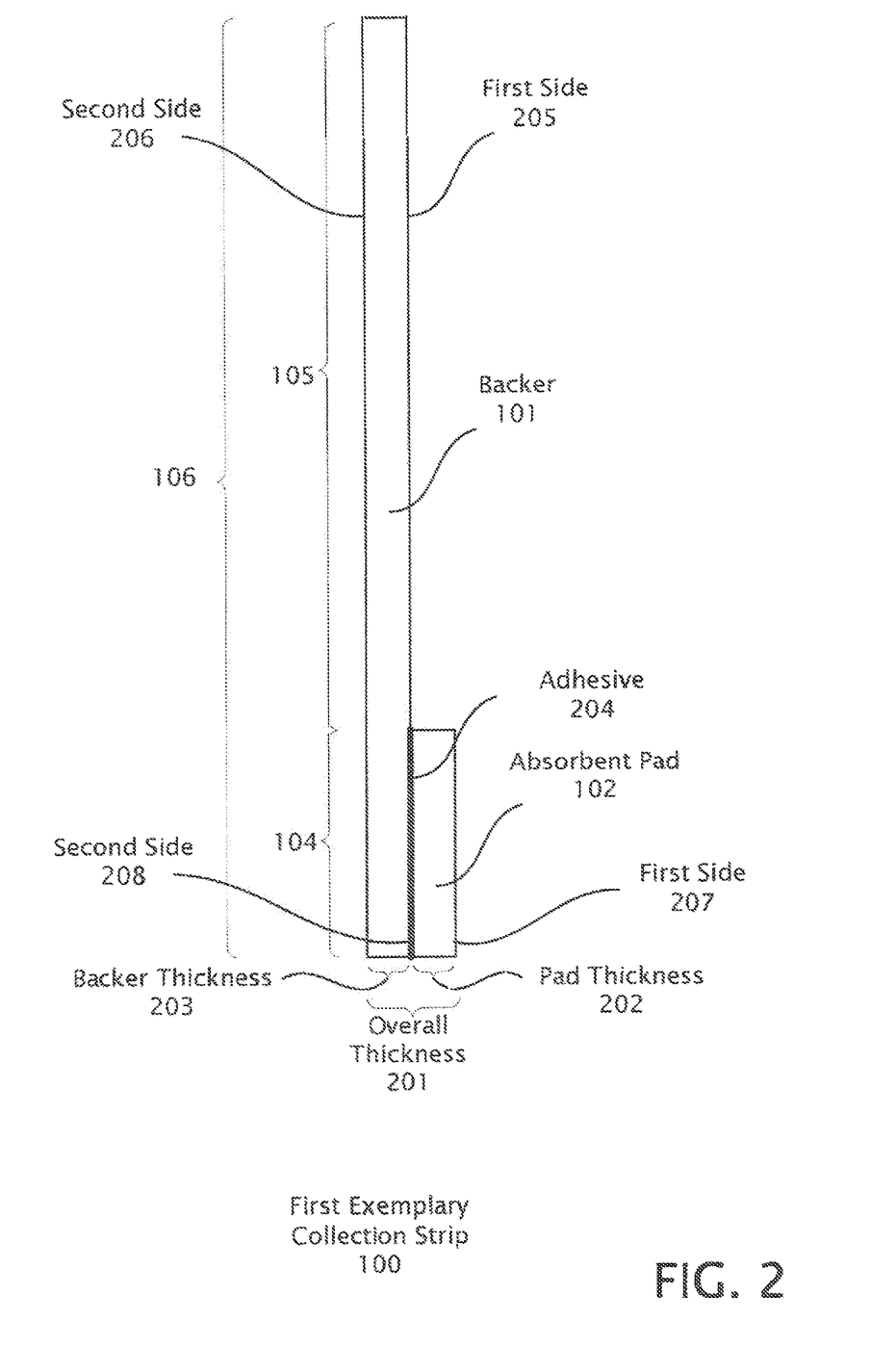
FIG. 2 is a diagram showing the side view of the first exemplary collection strip having a single pad.

FIG. 2 is a diagram showing the side view of the first exemplary collection strip having a single pad 100. The second side 206 of the backer 101 is generally blank, and may be used for additional labeling.

On the first side 205 of the backer 101 the absorbent pad 102 is disposed at or near the end of the backer 104. The absorbent pad 102 may include a first side 207 to which the sample may be applied. The absorbent pad 102 may also include a second side 208 which may be disposed against the first side 205 of the backer 101. The second side 208 of the absorbent pad 102 may be affixed to the first side 205 of backer 101 by a suitable adhesive 204 selected to not affect the testing or to release during processing, as is known to those skilled in the art. Alternatively, the absorbent pad may be fused directly to the backer 101 by techniques known to those skilled in the art.

The absorbent pad 102 typically has known absorption properties, and may have a more or less uniform pad thickness 202. When taken into consideration with the width (103 of FIG. 1) and height (104 of FIG. 1), the volume of the pad tends to collect a substantially known sample quantity suitable for subsequent testing.

In an alternative example of the first exemplary collection strip 100, an additional pad (not shown) may be disposed in any convenient location on the second side 206 of the backer 101. Such an additional collection strip may be of the same material as absorbent pad 102 to pick up additional sample material, or it may be of a differing material to perform a differing function.

Figure 3:
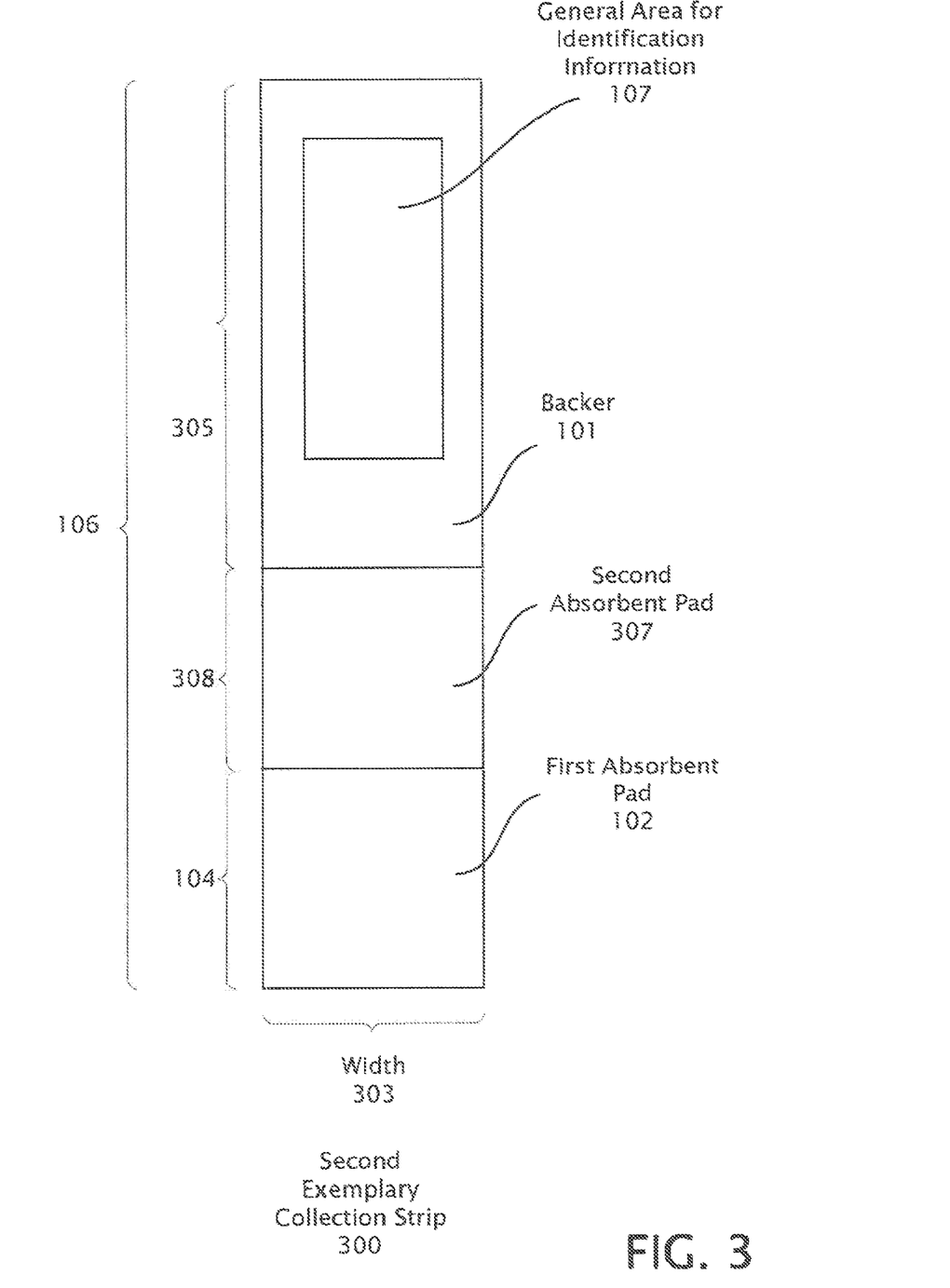
FIG. 3 is a diagram showing a front view of the second exemplary collection strip having two pads.

FIG. 3 is a diagram showing a front view of a second exemplary collection strip having two pads 300. Except for the additions herein, the construction is as previously described and as indicated by like reference numbers. In this collection strip 300 there may be two or more pads disposed at the end of the backer 101, where the bottommost pad(s) may be used for sample application, and physical or chemical treatment. The bottommost pad may be a selective or exclusionary material such as CYTOSEP®, or a matrix such as glass fiber that has been treated with a selective binding ligand such as antibody or nucleic acid sequence, or a reactive agent such as thrombin. For example, a material applied to the bottommost pad might be one having a specified pore size and may be used to filter blood before collection. CYTOSEP® or its equivalent is an example of a trademarked product that is capable of separating out red blood cells from the associated plasma. Or, as an example of a treatment, the bottommost pad 102 may be a thrombin impregnated pad that may cause clotting and retention of any un-clotted fibrinogen. Finally, an antibody, DNA sequence or other ligand that allows a different analyte of interest to pass through may be applied to the lower pad as well. After being drawn through the first pad 102, the sample, or treated sample, (e.g., plasma or serum) is collected in the second, or subsequent, pad 307 which can be of known volume if having a fixed or specified volume may be needed for the assay.

In the receiving lab, such a strip 307 can be collected, the lower pad 102 separated, cut off, or peeled off, and discarded, and the strip 101 with the upper pad 307 placed into a tube containing an appropriate elution buffer.

The initial capture pad 102 can be any kind of capture or retention mechanism, including chemical, physical, immunological capture, or change the specimen by any of several means (e.g., chemical, convert plasma to serum, pH, glycosylation, enzymatic modification or activation with a genetic, chemical or biological activator). The material of the first 102, and second 307 absorbent pad may also be the same as previously described for the first absorbent pad 102 in FIGS. 1-2.

The configuration may also allow separation of one or more components into separate pads, allowing for the analysis of both (or more in the case of more pads) pads for their respective elements that may be retained. For example, in the first pad 102, antibody against a specific analyte might be bound that would trap that analyte while letting other similar (but immunologically distinct) antigens pass to the second pad 307, but antibodies from both pads could be subsequently eluted under low pH and re-assayed in separate assays.

In another example, the first pad 102 might be treated with certain antigens or nucleic acid or biomarkers so as to retain or "scrub" certain kinds of antibodies or biomarkers (e.g., high affinity antibodies, or certain DNA or RNA sequences) stabilizing, or preserving agent and allow to pass through other antibodies biomarkers or nucleic acid sequences possibly with stabilizing agents of interest to the final specimen capture pad 307.

The multi-pad configuration 300 may be used for the collection of a blood or plasma specimen to detect fibrinogen degradation products (FDP), which are a biomarker for certain cancers. The challenge with such an analyte is that they are present with intact fibrin and fibrinogen which may confound the assay used to detect FDP. With the invention, thrombin and other clotting factors can be impregnated into the lower absorbent pad 102, which is the first recipient of the blood or plasma specimen. The thrombin and factors enable any remaining fibrinogen to clot in the first pad substantially retaining such fibrinogen and fibrin, but not retaining FDP. Alternatively, an antibody specific for a degradation site that results in FDP, but that does not recognize the FDP after degradation, could be bound to the first pad 102. In either case, the sample that then absorbs into the second upper pad 307 is typically substantially free of fibrin and fibrinogen, but not FDP; and a lab testing of such a strip for FDP, can simply peel off the lower pad 102 containing the fibrinogen fibrin that has been clotted and extract the upper pad 307 containing FDP in that pad, and then assay the resulting eluted buffer with minimal contamination of fibrinogen/fibrin.

An even more efficient sample might be obtained by the use of 3 pads disposed in line with each other, with the lower pad 102 containing the clotting factors, a second (middle) pad 307 composed of CYTOSEP® or similar blood cell and fibrin retention material, with the third pad (not shown) being the reservoir for the desired sample.

Figure 4:
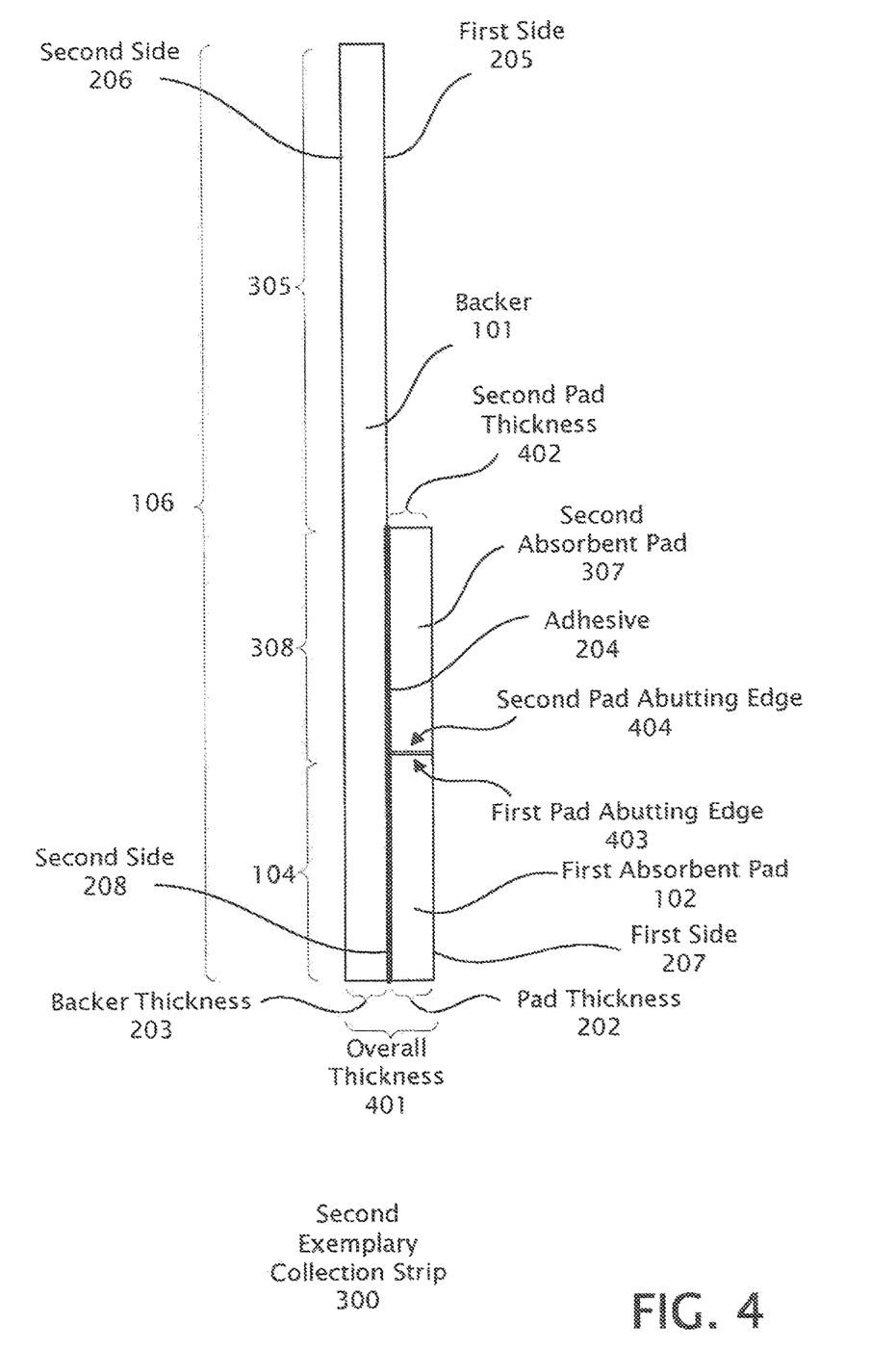
FIG. 4 is a diagram showing a side view of the second exemplary collection strip having two pads.

FIG. 4 is a diagram showing a side view of a second exemplary collection strip having two pads 300. In this example, a second absorbent pad 307 has been added to the previously described collection strip (100 of FIG. 1 and FIG. 2). The thickness 402 of the second absorbent pad 307 is selected to be appropriate for collecting a desired volume of sample material. However, this thickness is exemplary, and not meant to be limiting as other pad thicknesses may be called for depending upon the test to be performed.

The first and second absorbent pads have narrow edges 403, 404 that abut each other as shown. Neither the first pad 102, or the second absorbent pad 307 laps or folds over the top 207 of, or underneath the other to contact the second side 208. That is, the first side 207 of the first pad 102 does not overlap the second side 208 of the second pad 307, and vice versa. The pads are disposed in a common plane with a sample being drawn into an edge of the second pad 404 from the abutting edge 403 of the first pad. The pads 102, 307 are of substantially the same thickness. However, in alternative examples they may be of differing height. And, the sample is still drawn through the edges 403, 404 of abutting pads 102, 307. The abutting pads do not overlap, and typically do not utilize adhesive to couple one pad to the other, the edges typically simply touch.

Although the pads 302 and 207 are shown abutting each other, in equivalent examples the pads may be separated from each other and not touching. Also, it will be realized that the pads 307, 102 dimensions (length, width, height) need not be the same as each other, as differing dimensions and shapes may be equivalently provided. Also, it will be realized that the pad shape though shown rectangular may be square, rectangular, circular, oval or the like.

Although two pads are shown, the reader will realize that a plurality of pads may be provided, as desired for performing a particular test or tests.

The second exemplary collection strip 300 includes the previously described backer 301 that may have a thickness 403 sufficient to support the pads 102, 307. The thickness is exemplary, and not meant to be limiting in the thickness. In general, the thickness of the material 301 is selected to provide a sufficiently rigid and durable surface for pads 302, 307 during collection and processing. Material 301 is typically supplied as "sheet goods" from which strips are cut. Such material 301 is typically not molded but pressed flat, or rolled flat in the manufacturing process. In alternative examples, the backer 301 may be a laminate or composite of a plurality of suitable materials.

First absorbent pad 305 has an exemplary thickness 402 that in conjunction with its width, height and absorbance tends to define the sample volume collected.

Figure 5:
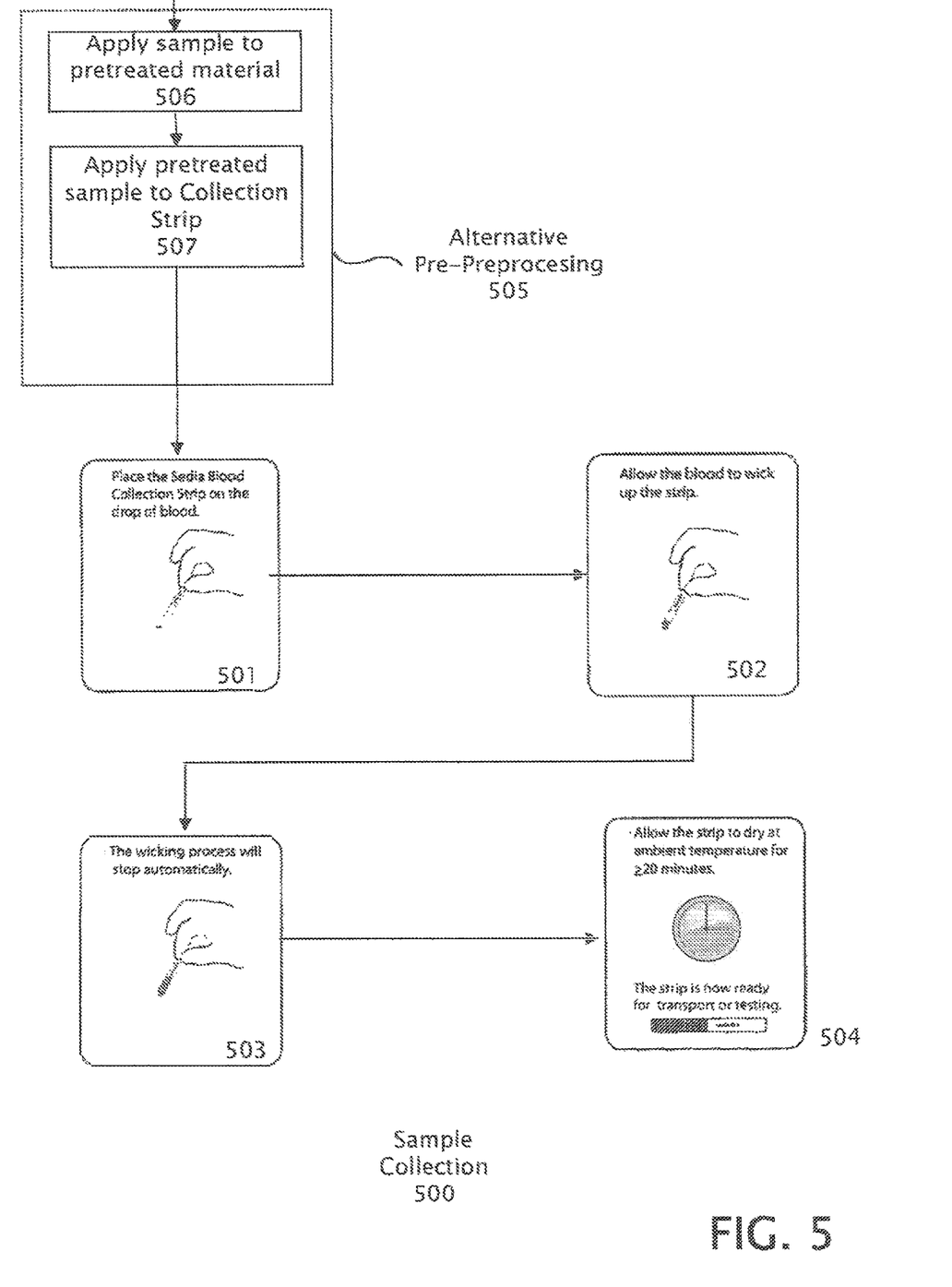
FIG. 5 illustrates a process of collecting a sample using one of the exemplary collection strips described herein.

FIG. 5 illustrates a process of collecting sample using one of the exemplary collection strips described herein. In this exemplary process a blood sample is being collected. However, it will be recognized by those skilled in the art that the process described applies to other types of biological samples as well.

A blood specimen collected with the exemplary collection strips (100 of FIG. 1 or 300 of FIG. 3) typically dries quickly and in as little at 20 minutes in some conditions.

The exemplary collection strips (100 of FIG. 1 or 300 of FIG. 3) are cost effective. They are less expensive than the typical collection card per specimen and require no preparation or cutting prior to or after their use.

A sample, such as a blood sample, is dropped, onto the absorbent pad 501. The sample is applied so that it wicks up or saturates the absorbent pad 502 so that a predetermined known volume of sample is collected since the wicking process stops automatically 503 once the pad absorbs all that it can. The sample is then dried at ambient or elevated temperature until the pad is dry, and ready for transport or testing 504. The pad may also be stored or archived if desired.

In an alternative example of the collection 505, the collection site can perform pre-processing, or pre-treating, of the sample prior to addition of the sample to the sample strip. In this example, the second exemplary collection strip (300 of FIG. 3) may be useful, as the first absorbent pad (102 of FIG. 3) contacting the sample may perform the pretreating, while the second absorbent pad (307 of FIG. 3) above and contacting the first absorbent pad (102 of FIG. 3) collects the pretreated sample. For example, use of a porous frit or filter (e.g. POREX™, filter paper, etc.) in a flow-through tube where the porous material might have a pretreatment material, that the sample is first forced through 506, and then touched directly to the sample strip containing one or more pads 507. For example, the porous material could be the clotting agents and thrombin which when a blood or plasma sample is added and forced through, allows more thorough clotting prior to absorption onto the sample strip. The porous material could be used as a first sample collection material which when placed into a syringe-like container, is compressed or washed to extract out the material onto the receiving pad of the invention device.

Figure 6:
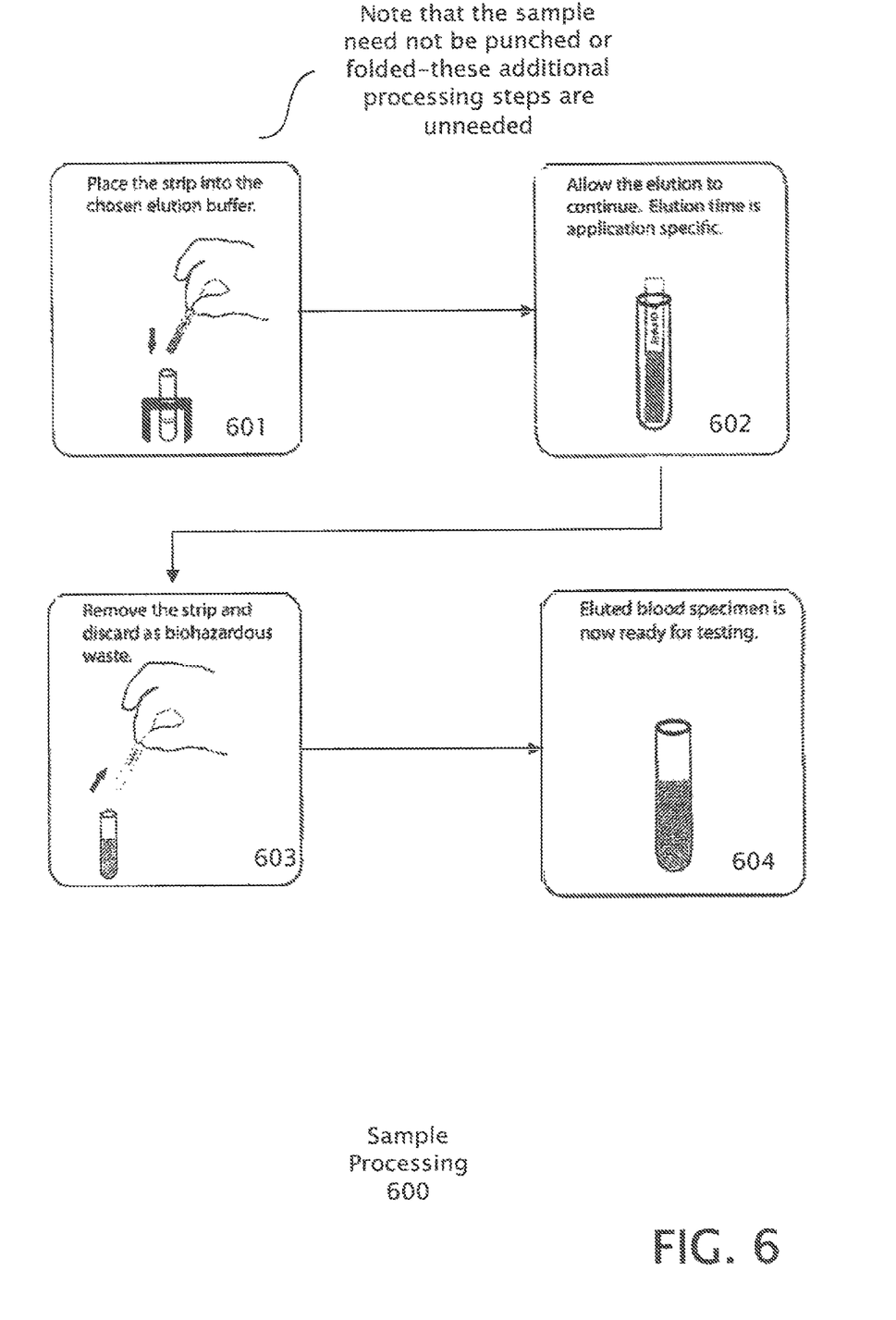
FIG. 6 illustrates a process of preparing a dried sample for collection using one of the exemplary collection strips described herein.

FIG. 6 illustrates a process of preparing a dried sample for testing 600 using one of the exemplary collection strips described herein. The dried pad is transported (e.g., by mail) to a central laboratory or other processing location, where the strip is removed from the transport packaging and placed into a tube containing a buffer or diluent 601.

Typically, the assay sample diluent may contain salts and buffer of suitable pH, but may also contain additional detergents, blocking agents, enzymes, or precipitating agents to elute the analyte of interest. For example, the analyte of interest may be antibodies to a specific agent such as HIV, Hepatitis B or C, syphilis, influenza, etc., or a disease marker such as the infectious agent itself, or cancer markers (e.g., CEA, AFP, RECAF, CA-125, PSA, etc.), hormone, drug, DNA, or RNA.

The collection strip is allowed to elute for a period of time that is application specific, as known to those skilled in the art 60. Next the collection strip is removed and discarded, typically as bio-hazardous waste 603. The eluted specimen in the tube is now ready for testing 604.

In the process described above using either the first or second exemplary collection strips (100 of FIG. 1 or 300 of FIG. 3), the blood specimen quickly elutes from either the first or second exemplary collection strips (100 of FIG. 1 or 300 of FIG. 3) allowing for same-day testing without the inconvenient overnight elution process that is typical in current processes.

Eluting blood from the first or second exemplary collection strips (100 of FIG. 1 or 300 of FIG. 3) is a simple one-step process of placing the strip into the elution tube, easily holding the strip at the label end between user's fingers 601. In contrast, eluting blood from a conventional dried blood spot card typically requires the use of a hole puncher to obtain a disk, then tediously transferring that disk into the elution buffer using forceps.

In this unique process there is no potential for cross-contamination when using the first or second exemplary collection strips (100 of FIG. 1 or 300 of FIG. 3). The dried specimen on the first or second exemplary collection strips (100 of FIG. 1 or 300 of FIG. 3) is not placed in contact with anything between contact of the strip with the specimen source until it undergoes elution.

In contrast, a specimen collected with a conventional collection card risks cross-contamination through the hole puncher and the forceps which are in contact with many specimens, usually without cleaning in between use. In addition, common hole punchers can vary from lab to lab giving different sample sizes causing inter-lab variability of result. For example, the most common size punch is a ¼"/6 mm punch which may in fact be 6 mm in diameter or 6.35 mm (0.25 inch) diameter, a difference in area or 12%. This variability introduced into the conventional process is eliminated by the processing method described above.

Figure 7:
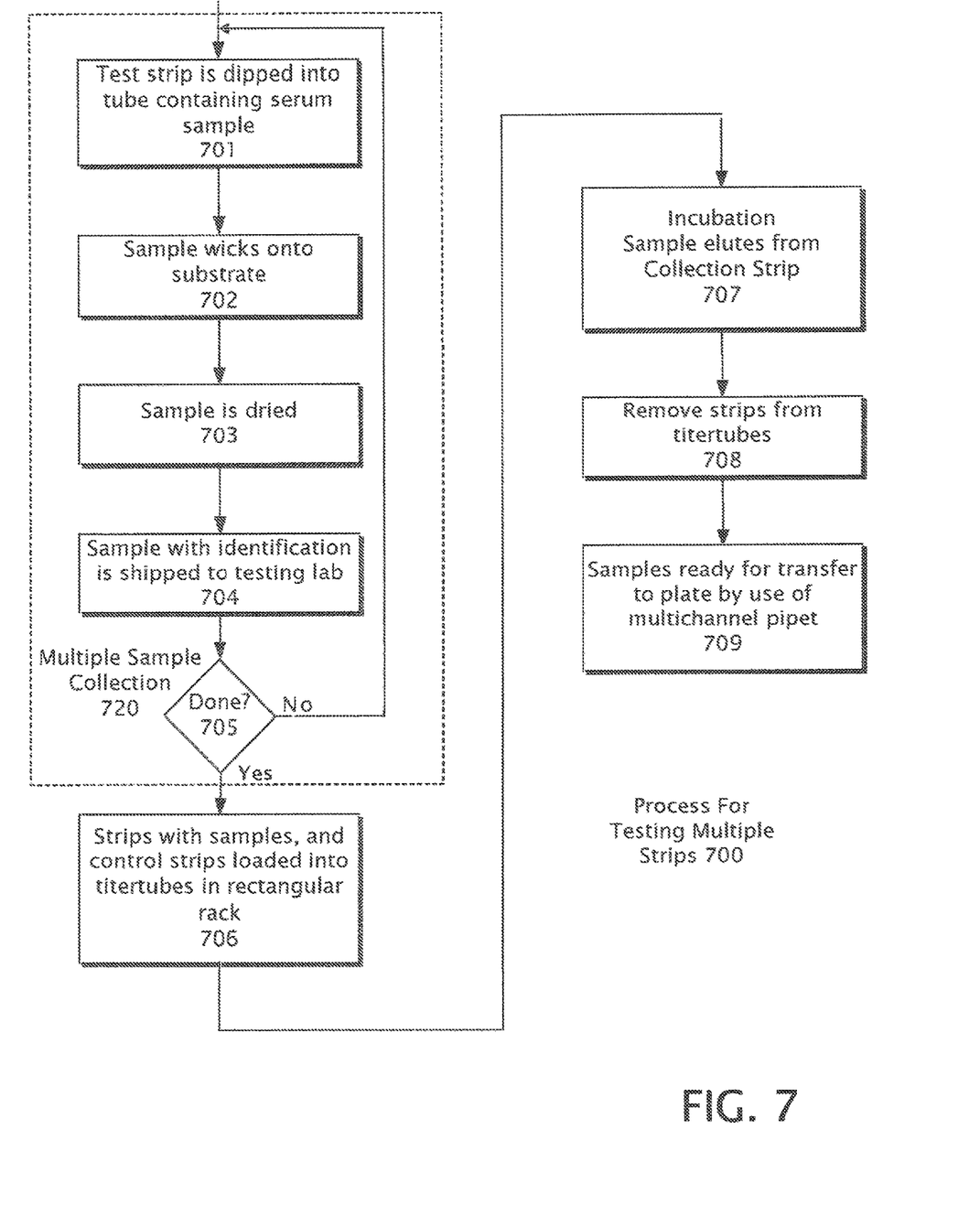
FIG. 7 is a process flow diagram for the processing of multiple specimens utilizing the exemplary collection strips described herein.

FIG. 7 is a process flow diagram for the processing of multiple specimens 700 utilizing the exemplary collection strips described herein. In this process 700, multiple samples on a plurality of collection strips may be collected 720, and processed in a batch to speed processing. In particular, this process eliminates the typical step of punching, or otherwise separating a sample from a specimen card. Likewise, folding or other manipulation of the sample is not performed. Such a process also may introduce cross contamination during the punching process. By even eliminating the step of separating samples, batch testing can be sped up considerably.

At block 701 a collection strip may be dipped into a tube or other receptacle containing a serum, or other type of sample, on which testing is to be performed. Alternatively, the sample may be applied directly to the collection strip when collected. For example, a finger may be lanced, and the blood produced may be applied directly to the test strip without the need for collecting the blood in a vial first.

At block 702 the sample wicks onto the absorbent pad (102 of FIG. 1) saturating it. Advantageously, the pad of known dimensions and absorbing characteristics tends to provide a sample of a known volume due to its absorption characteristics.

At block 703 the sample is dried. If the sample is taken from a vial, the strip is removed, allowing it to dry. In the case of direct collection, air or forced air, or possibly heat, may be used to dry the sample, provided that the method of drying will not damage the sample, or otherwise impair the testing to be done.

At block 705, if more samples are to be collected and the sampling is not yet done, the process is repeated, collecting multiple samples. When collection of samples is completed, the samples may next be prepared for testing 706, 707, 708.

To allow testing, the dried samples must typically be present in liquid form. An appropriate solvent or other substance to release sample material from the collection strip may be employed.

At block 706, the collection strips have been received by the lab and have been arranged in conventionally constructed titertubes and placed in a tack or test block. An 8×12 pattern with even spaces between the vial positions is typical for such test blocks. However other patterns may be utilized. In testing, a control sample or calibration sample may often be included to calibrate the system. Accordingly, in this collection set up a collection strip, or strips for calibration purposes, may be included in the batch.

At block 707 an incubation period is provided to allow the sample to elute from the test material. Typically for testing, a known time is used so that sufficient material from the collection strip is transferred into solution with the desired solvent. In the exemplary case of testing blood, serum elutes from the collection material into the liquid.

At block 708 the strips are removed from the tubes, so that the sample may be further processed. The strips provide handles with the backing material, and do not need to be retrieved by dipping an instrument into the liquid in the vial, eliminating another slow process that could cause cross contamination.

At block 709 the liquid samples are prepared and are ready for batch testing. Sample material may be removed from a row in a single operation by using a conventional multichannel pipette with the number of channels matching the number of samples in a row. After being drawn into the multichannel pipette, the samples may be transferred to a plate, such as an exemplary ELISA plate, where the testing is performed and the results recorded or otherwise processed. Those skilled in the art will realize that the process may be further automated so that the collection strips may be loaded into a dedicated machine, with barcode or other methods used to identify the samples to the machine, where the processing as described above may be done robotically with the results reported to a computer memory, or transmitted over a networked computer system so that the results may be used to map incidence of illness, or otherwise be used to map trends of epidemics, automate reporting, or categorization of the results, and the like.

Additional advantages of the invention include (1) the fact that the device can fit into titertubes in an 8×12 configuration such that the eluted specimen may be easily be transferred to a standard EIA plate or other size plate configurations (e.g., 384 well plates); (2) The elongate backer is made from a sheet material that is typically pressed or rolled, which is much more cost effective than molded materials such as pipettes are made of, since no cavity needs to be formed in the backer; (3) lower cost (4) eliminates the need to punch out a specimen using special tools; (5) enables the dried specimen to be labeled with sample information and for the dried specimen to retain this information during elution (a dried spot will lose the linkage as soon as the spot is punched) significantly reducing the risk of cross contamination from punching or handling equipment; (6) the dried specimen can be put into the elution tube without the need of forceps or touching the dried specimen; (7) treatments and/or trapped and unwanted entities can be removed from the strip prior to elution (e.g., by tearing off the bottom pad(s); (8) that capacity of the collection material dictates how much specimen is collected and that volume is consistent for all specimens collected per specimen type; (9) cross contamination risk reduced or significantly eliminated with dried blood strips as handling with a paper punch or forceps is not required; and (10) the absorbent pad material can be selected from multiple options based on non-binding characteristics at blood analyte of interest.

Those skilled in the art will realize that the process sequences described above may be equivalently performed in any order to achieve a desired result. Also, sub-processes may typically be omitted as desired without taking away from the overall functionality of the processes described above.

The invention claimed is:

1. A method for testing a blood sample comprising:
applying a blood sample to a blood collection device, which device comprises a flat elongated rectangular backer having a first end where identifying information is disposed, a first absorbent pad disposed at a second end of the flat rectangular elongated backer and a second absorbent pad disposed between the first absorbent pad and the first end of the flat elongated rectangular backer and in contact with the first absorbent pad, wherein, both the first absorbent pad and the second absorbent pad reside on the same flat elongated rectangular backer, and the blood sample is applied to the first absorbent pad and then flows laterally into the second absorbent pad;
drying the blood sample in the second absorbent pad;
removing the first absorbent pad from the blood collection device after the blood sample flows laterally into the second absorbent pad;
eluting the dried blood sample from the second absorbent pad into an elution buffer; and
testing the eluted blood sample.

2. The method for testing a blood sample of claim 1, further comprising pre-processing by filtering the blood sample prior to applying it to the first absorbent pad.

3. The method for testing a blood sample of claim 2, in which filtering is performed by flowing the blood sample laterally from the first absorbent pad into the second absorbent pad.

4. The method for testing a blood sample of claim 3, in which the second absorbent pad is treated.

5. The method for testing a blood sample of claim 4, in which the second absorbent pad is a selective or exclusionary material membrane, whereby red blood cells are excluded from the sample in the second absorbent pad.

6. The method for testing a blood sample of claim 4, in which the treatment is thrombin, whereby retention and clotting of any previously un-clotted fibrinogen is caused.

7. The method for testing a blood sample of claim 1, which is conducted to detect fibrinogen degradation products (FDP) in the blood sample.

8. The method for testing a blood sample of claim 1, which is conducted to detect antibodies to a specific agent, a disease marker, a cancer marker, a hormone, a drug, a DNA, or an RNA in the blood sample.

9. The method for testing a blood sample of claim 1, which is conducted on a control sample or a calibration sample.

10. The method for testing a blood sample of claim 1, wherein the dried blood sample is eluted from the second absorbent pad into an elution buffer in a tube containing the elution buffer.

* * * * *